United States Patent [19]

Ortyl et al.

[11] Patent Number: 5,574,045

[45] Date of Patent: Nov. 12, 1996

[54] ORAL PHARMACEUTICAL COMPOSITION OF PIPERIDINOALKANOL COMPOUNDS IN SOLUTION FORM

[75] Inventors: Thomas T. Ortyl, Kansas City, Mo.; Paul F. Skultety, Leawood; Gail H. Hurst, Stilwell, both of Kans.

[73] Assignee: Hoechst Marion Roussel, Inc., Cincinnati, Ohio

[21] Appl. No.: 469,392

[22] Filed: Jun. 6, 1995

[51] Int. Cl.$^6$ .................................................. A61K 31/445
[52] U.S. Cl. ................................................................ 514/317
[58] Field of Search ............................................. 514/317

[56] References Cited

U.S. PATENT DOCUMENTS

| | | | |
|---|---|---|---|
| 3,806,526 | 4/1974 | Carr et al. | 260/293.64 |
| 3,878,217 | 4/1975 | Carr et al. | 260/293.64 |
| 3,966,949 | 6/1976 | Webb | 424/250 |
| 4,254,129 | 3/1981 | Carr et al. | 424/267 |
| 4,254,130 | 3/1981 | Carr et al. | 424/267 |
| 4,285,957 | 8/1981 | Carr et al. | 424/267 |
| 4,285,958 | 8/1981 | Carr et al. | 424/267 |
| 4,929,605 | 5/1990 | Domet et al. | 514/54 |
| 4,966,061 | 2/1991 | Webb et al. | 424/475 |
| 4,999,226 | 3/1991 | Schock et al. | 424/472 |
| 5,049,568 | 8/1991 | Kristof et al. | 514/317 |

FOREIGN PATENT DOCUMENTS

| | | |
|---|---|---|
| 0111114 | 10/1983 | European Pat. Off. . |
| 0173293 | 8/1985 | European Pat. Off. . |

OTHER PUBLICATIONS

Jones, A. R., Australian J. of Pharmacy, pp. 178–181 (1982).
Yalkowsky et al., J. of Pharmaceutical Sciences, vol. 74, No. 4, pp. 416–421 (1985).

*Primary Examiner*—Raymond Henley, III
*Assistant Examiner*—William R. A. Jarvis
*Attorney, Agent, or Firm*—Nelsen L. Lentz

[57] ABSTRACT

The present invention provides an oral pharmaceutical composition in solution form, comprising,
  a) a therapeutically effective amount of a piperidinoalkanol compound or a pharmaceutically acceptable salt thereof; and
  b) a suitable solvent systems, comprising propylene glycol and glacial acetic acid.

10 Claims, No Drawings

ORAL PHARMACEUTICAL COMPOSITION OF PIPERIDINOALKANOL COMPOUNDS IN SOLUTION FORM

BACKGROUND OF THE INVENTION

It has been established that various piperidinoalkanol compounds are useful as antihistamines, antiallergy agents and bronchodilators as disclosed in U.S. Pat. Nos. 3,878,217, 4,254,129 and 4,285,957. Examples of representative formulations of these various piperidinoalkanol compounds are described below.

In U.S. Pat. No. 4,929,605, J. Domet and D. Shah describe a pharmaceutical composition in solid unit dosage form, comprising, a therapeutically effective amount of a piperidinoalkanol compound, or a pharmaceutically acceptable salt thereof, a pharmaceutically acceptable nonionic or cationic surfactant in an amount of from about 0.1% to about 6% by weight of the composition, and a pharmaceutically acceptable carbonate salt in an amount of from about 2% to about 50% by weight of the composition.

N. Webb and G. Hammer describe in U.S. Pat. No. 4,996,061, a pharmaceutical composition in the form of a multiple-compression tablet comprising a discrete zone made from a formulation which provides sustained-release of a therapeutically effective decongestant amount of a sympathomimetic drug and a discrete zone made from a different formulation which provides immediate release of a therapeutically effective antihistaminic amount of a piperidinoalkanol and, optionally, a therapeutically effective decongestant amount of a sympathomimetic drug.

Kristof et al. describe in U.S. Pat. No. 5,049,568, a liquid pharmaceutical composition comprising (a) a piperidinoalkanol in an amount of from about 2 to about 25 mM; (b) a suitable buffer, selected from the group consisting of gluconic acid buffer, lactic acid buffer, citric acid buffer and acetic acid buffer, in an amount of from about 0.0001 to about 0.5 M; and (c) water in an amount of from about 5% to about 99% by weight of the composition.

Efforts have focused on improving the bioavailability of various piperidinoalkanol compounds in order to improve their therapeutic efficiency. The present invention relates to a novel oral pharmaceutical composition for various piperidinoalkanol compounds, or their pharmaceutically acceptable salts, in solution form which provides efficient and immediate absorption, and bioavailability of these compounds.

SUMMARY OF THE INVENTION

The present invention provides an oral pharmaceutical composition in solution form, comprising,
a) a therapeutically effective amount of a piperidinoalkanol compound or a pharmaceutically acceptable salt thereof; and
b) a suitable solvent system.

The invention further provides an oral pharmaceutical composition in solution form, comprising,
a) a therapeutically effective amount of a piperidinoalkanol compound or a pharmaceutically acceptable salt thereof; and
b) a suitable solvent system, the solvent system comprising about 95.0% to about 99.9% propylene glycol by weight of the solvent system and about 0.1% to about 5.0% of glacial acetic acid by weight of the solvent system.

DETAILED DESCRIPTION OF THE INVENTION

As used herein the terms "piperidinoalkanol compounds" and "piperidinoalkanol compounds and their pharmaceutically acceptable salts" refers to those compounds described by formulas (I), (II), (III) and (IIIa) which are disclosed in U.S. Pat. Nos. 3,878,217, 4,254,129 and 4,285,957 the disclosure of each patent being incorporated herein by reference.

Piperidinoalkanol compounds of formula (I) are those which correspond to the formula;

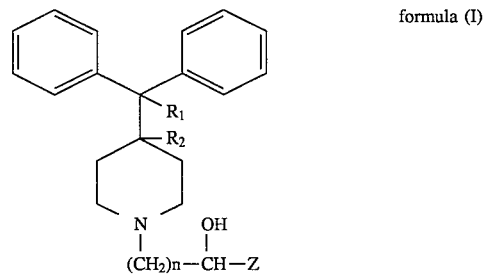

formula (I)

wherein $R_1$ is hydrogen or hydroxy; $R_2$ is hydrogen; or $R_1$ and $R_2$ taken together form a second bond between the carbon atoms bearing $R_1$ and $R_2$; n is a positive whole integer of from 1 to 3; Z is thienyl, phenyl or substituted phenyl wherein the substituents on the substituted phenyl may be attached at the ortho, meta or para positions of the unsubstituted phenyl ring and are selected from the group consisting of a halogen atom, a straight or branched lower alkyl chain of from 1 to 4 carbon atoms, a lower alkoxy group of from 1 to 4 carbon atoms, a di(lower)alkylamino group, or a saturated monocyclic heterocyclic ring selected from the group consisting of pyrrolidino, piperidino, morpholino, or N-(lower)alkylpiperazino, or pharmaceutically acceptable acid addition salts thereof.

Piperidinoalkanol compounds of formula (II) are those which correspond to the formula;

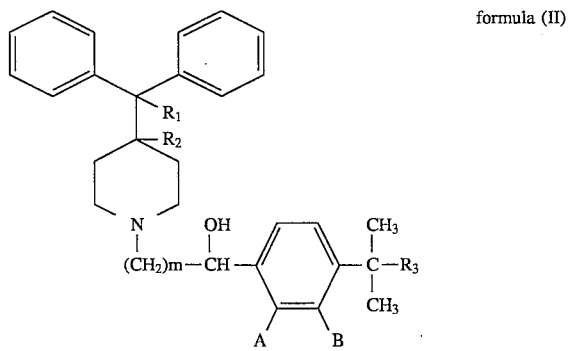

formula (II)

wherein $R_1$ represents hydrogen or hydroxy; $R_2$ represents hydrogen; or $R_1$ and $R_2$ taken together form a second bond between the carbon atoms bearing $R_1$ and $R_2$; m is an integer of from 1 to 5; $R_3$ is —$CH_3$, or —$CH_2OH$; each A and B is hydrogen or hydroxy; with the provisos that at least one of A or B is hydrogen and one of A or B is other than hydrogen when $R_3$ is —$CH_3$; and pharmaceutically acceptable salts and individual optical isomers thereof.

Piperidinoalkanol compounds of formula (III) are those which correspond to the formula;

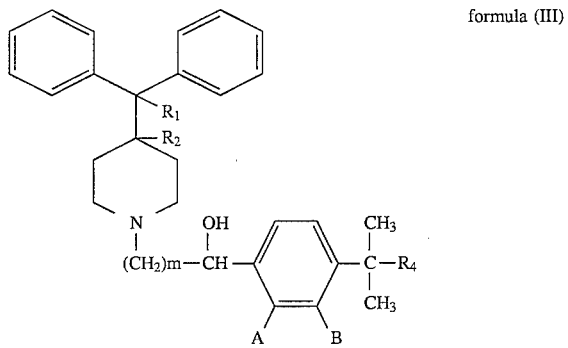

formula (III)

wherein $R_1$ represents hydrogen or hydroxy; $R_2$ represents hydrogen; or $R_1$ and $R_2$ taken together form a second bond between the carbon atoms bearing $R_1$ and $R_2$; m is an integer of from 1 to 5; $R_4$ is —$CO_2H$ or —$CO_2$alkyl wherein the alkyl moiety has from 1 to 6 carbon atoms and is straight or branched; each of A and B is hydrogen or hydroxy; with the proviso that at least one of A or B is hydrogen; and pharmaceutically acceptable salts and individual optical isomers thereof.

4-[4-[4-(Hydroxydiphenylmethyl)-1-piperdinyl]-1-hydroxybutyl]-α,α-dimethylbenzeneacetic acid hydrochloride of formula (IIIa)

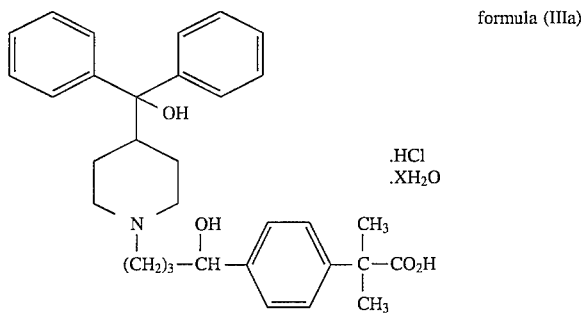

formula (IIIa)

wherein X is a number ranging from about zero to 5, and the individual optical isomers thereof, is the preferred piperidinoalkanol compound. The compound 4-[4-[4- (Hydroxydiphenylmethyl)-1-piperdinyl]-1-hydroxybutyl]-α,α-dimethylbenzeneacetic acid hydrochloride is the most preferred piperidinoalkanol compound wherein X is zero in formula (IIIa).

Illustrative examples of straight or branched alkyl groups having from 1 to 4 carbon atoms referred to herein are methyl, ethyl, n-propyl, isopropyl, n-butyl, isobutyl and t-butyl. Illustrative examples of straight or branched alkyl groups having from 1 to 6 carbon atoms referred to herein are methyl, ethyl, n-propyl, isopropyl, n-butyl, isobutyl, t-butyl, n-pentyl, cyclopentyl, n-hexyl and cyclohexyl. Illustrative examples of lower alkoxy groups of from 1 to 4 carbon atoms referred to herein are methoxy, ethoxy, propoxy, n-butoxy, isobutoxy, sec-butoxy and t-butoxy. The terms "halo", "halogen" or "halide" refers to a fluorine, chlorine, bromine or iodine atom. As used herein the term "strength" refers to the concentration of the piperidinoalkanol compounds of formulas (I), (II), (III) and (IIIa) in the pharmaceutical composition in solution form wherein the concentration is expressed as milligrams of the piperidinoalkanol compound of formulas (I), (II), (III) or (IIIa) per milliliter of suitable solvent system (mg/mL).

The term "pharmaceutically acceptable salt" refers to those salts of formulas (I), (II), (III) and (IIIa) that are not substantially toxic at the dosage administered to achieve the desired effect and do not independently possess significant pharmacological activity. The salts included within the scope of this term are pharmaceutically acceptable acid addition salts of a suitable inorganic or organic acid. Suitable inorganic acids are, for example hydrochloric, hydrobromic, sulfuric and phosphoric acids. Suitable organic acids include carboxylic acids, such as acetic, propionic, glycolic, lactic, pyruvic, malonic, succinic, fumaric, malic, tartaric, citric, cyclamic, ascorbic, maleic, hydroxymaleic, dihydroxymaleic, benzoic, phenylacetic, 4-aminobenzoic, 4-hydroxybenzoic, anthranilic, cinnamic, salicylic, 4-aminosalicyclic, 2-phenoxybenzoic, 2-acetoxybenzoic and mandelic acid, sulfonic acids, such as methanesulfonic, ethanesulfonic and β-hydroxyethanesulfonic acid. In addition, pharmaceutically acceptable salts include those salts of formulas (I), (II), (III) and (IIIa) formed with inorganic and organic bases, such as those of alkali metals, for example sodium, potassium and lithium, alkaline earth metals, for example calcium and magnesium, light metals of group IIIA, for example aluminum, organic amines, for example primary, secondary or tertiary amines, such as cyclohexylamine, ethylamine, pyridine, methylaminoethanol and piperazine. The salts are prepared by conventional means by one of ordinary skill in the art as, for example, by treating a compound of formulas (I), (II), (III) or (IIIa) with an appropriate acid or base. Such salts can exist in either a hydrated or substantially anhydrous form.

As used herein the term "inert ingredient" refers to those therapeutically inert ingredients that are well known in the art of pharmaceutical science which can be used singly or in various combinations, and include, for example, sweetening agents, coloring agents, flavoring agents, antioxidants, solubilizing agents, and the like, as are disclosed in The United States Pharmacopeia, XXII, 1990, (1989 The United States Pharmacopeial Convention, Inc.), pages 1857–1859, which is incorporated herein by reference. It is well recognized and appreciated by one of ordinary skill in the art that the pharmaceutical composition of the present invention may contain the above inert ingredients in various amounts and combinations.

The pharmaceutical composition of the present invention is administered orally in the form of a solution in a unit dose. A unit dose is that amount of the pharmaceutical composition which is individually administered in solution form. A unit dose of the pharmaceutical composition is individually administered by the use of techniques well known to one of ordinary skill in the art, such as a unit dose oral syringe. The oral pharmaceutical compositions of the present invention are useful in providing a solution of a piperidinoalkanol compound of formulas (I), (II), (III) or (IIIa) which can be administered orally to a patient in need of treatment with an antihistaminic agent, antiallergy agent or bronchodilator.

As used herein, the term "patient" refers to a warm-blooded animal, such as a mammal, which is in need of an antihistamine, antiallergy agent or bronchodilator. It is understood that humans, dogs, mice and rats are included within the scope of the term "patient".

A therapeutically effective amount can be readily determined by the attending diagnostician, as one skilled in the art, by the use of known techniques and by observing results obtained under analogous circumstances. In determining the therapeutically effective amount or dose, a number of factors are considered by the attending diagnostician, including, but not limited to: the species of mammal; its size, age, and general health; the response of the individual patient; the particular compound administered; the mode of administration; the bioavailability characteristics of the preparation administered; the dose regimen selected; the use of concomitant medication; and other relevant circumstances.

A therapeutically effective amount of a piperidinoalkanol compound of formula (I), (II), (III) or (IIIa) is that amount which produces the desired therapeutic response (i.e., antihistaminic, antiallergic or bronchodilatory effect) upon oral administration according to a single or multiple dosage regimen. A therapeutically effective amount of a piperidinoalkanol compound of formula (I), (II), (III) or (IIIa) may vary over a wide range from about 0.01 milligrams per kilogram (mg/kg) to about 20 (mg/kg) of body weight per dose. An oral pharmaceutical composition in solution form which provides from about 5 mg to about 360 mg of a piperidinoalkanol compound of formula (I), (II), (III) or (IIIa) per unit dose is preferred and those which provide from about 40 mg to about 240 mg per unit dose are most preferred.

The piperidinoalkanol compounds of formulas (I), (II), (III) and (IIIa) are readily prepared by one of ordinary skill in the art, for example, utilizing the techniques and procedures described in U.S. Pat. Nos. 3,878,217, 4,254,129 and 4,285,957.

Preparation of the oral pharmaceutical composition of the piperidinoalkanol compounds of formulas (I), (II), (III) and (IIIa) in solution form is readily performed by one of ordinary skill in the art. For example, a piperidinoalkanol compound of formulas (I), (II), (III) or (IIIa), such as 4-[4-[4-(hydroxydiphenylmethyl)-1-piperidinyl]-1-hydroxybutyl]-$\alpha,\alpha$-dimethylbenzeneacetic acid hydrochloride is dissolved in a suitable solvent system. The amount of piperidinoalkanol compound of formulas (I), (II), (III) or (IIIa) dissolved in the suitable solvent system can range from about 0.01 mg/mL to about 188 mg/mL of piperidinoalkanol compound, preferably about 2.5 mg/mL to about 133 mg/mL and most preferably about 15.0 mg/mL. Examples of a suitable solvent system are propylene glycol and glacial acetic acid, and the like. The preferred suitable solvent system is propylene glycol and glacial acetic acid. The composition by weight of the suitable solvent system comprising propylene glycol and glacial acetic acid can range from about 95.0% to about 99.9% by weight of propylene glycol, preferably about 98.0% to about 99.0% and most preferably 98.5% and from about 0.1% to about 5.0% by weight of glacial acetic acid, preferably about 1.0% to about 2.0% and most preferably 1.5%. Heat may be applied as needed to facilitate dissolution of the piperidinoalkanol compound into the suitable solvent system.

One skilled in the art of pharmaceutical science will recognize and appreciate that the oral pharmaceutical composition in solution form of the present invention may also contain therapeutically active ingredients other than the piperidinoalkanol compounds of formulas (I), (II), (III) or (IIIa). It is well known that antihistamines can beneficially be combined with certain decongestants, cough suppressants, expectorants and analgesic agents in a single dosage form. Many examples of such combination therapy products are commercially available. Likewise, the oral pharmaceutical composition in solution form of the present invention may be formulated to contain such decongestants as pseudoephedrine, phenylepherine and the like; such analgesic agents as aspirin, acetaminophen, ibuprofen and the like; such cough suppressants as dextromethorphan, codeine and the like; and expectorants such as guaifenesin and the like. Selection of one or more therapeutically active ingredients in addition to the piperidinoalkanol compounds of formulas (I), (II), (III) or (IIIa) and the amounts to be used can be readily determined by one skilled in the art by reference to standard procedures and practices, and the recommended dosage levels for the additional therapeutically active ingredients. Furthermore, one skilled in the art of pharmaceutical science will recognize and appreciate that many of these additional therapeutically active ingredients can be utilized in the form of their pharmaceutically acceptable salts. For example, pseudoephedrine HCl, phenylepherin HCl, dextromethorphan HBr, codeine phosphate, codeine sulphate and the like, can be used.

One of ordinary skill in the art would recognize that when preparing the oral pharmaceutical composition in solution form from an essentially anhydrous piperidinoalkanol compound, such as 4-[4-[4-(Hydroxydiphenylmethyl)-1-piperidinyl]-1-hydroxybutyl]-$\alpha,\alpha$-dimethylbenzeneacetic acid hydrochloride, the piperidinoalkanol compound may exist in various hydrated forms after being dissolved in the suitable solvent system.

The following examples are understood to be illustrative only and are not intended to limit the scope of the present invention in any way. As used herein, the following terms have the indicated meanings: "$m^2/g$" refers to square meters per gram and is used as a measurement of particle surface area; "kg" refers to kilograms; "g" refers to grams; "mmol" refers to millimoles; "ml" refers to milliliters; "bp" refers to boiling point; "mp" refers to melting point; "°C." refers to degrees Celsius; "°F." refers to degrees Fahrenheit; "mm Hg" refers to millimeters of mercury; "µL" refers to microliters; and "µg" refers to micrograms.

EXAMPLE 1

Preparation of an Oral Pharmaceutical Composition of
4-[4[4-(Hydroxydiphenylmethyl)-1-piperidinyl]-1-hydroxybutyl]- $\alpha,\alpha$-dimethylbenzeneacetic acid hydrochloride in Solution Form with a Strength of 22.5 mg/mL A solvent system of propylene glycol and glacial acetic acid with a composition of 98.5% propylene glycol and 1.5% glacial acetic acid by weight can be prepared by adding 1.5 g of glacial acetic acid to 98.5 g propylene glycol and mixing until a uniform solution is produced. Then dissolve 1.125 g of 4-[4-[4-(hydroxydiphenylmethyl)-1-piperidinyl]1-hydroxybutyl]-$\alpha,\alpha$-dimethylbenzeneacetic acid hydrochloride in 40 mL of the solvent system. Heat may be applied if needed to facilitate dissolution of 4-[4-[4-(hydroxydiphenylmethyl)-1-piperidinyl]-1-hydroxybutyl]-$\alpha,\alpha$dimethylbenzeneacetic acid hydrochloride. After dissolution is complete, add a sufficient amount of the solvent system to bring the total volume of the solution to 50 mL (q.s.), to provide the oral pharmaceutical composition in solution form with a strength of 22.5 mg/mL.

EXAMPLE 2

Preparation of an Oral Pharmaceutical Composition of
4-[4-[4-(Hydroxydiphenylmethyl)-1-piperidinyl]-1-hydroxybutyl]- $\alpha,\alpha$-dimethylbenzeneacetic acid hydrochloride in Solution Form with a Strength of 45.0 mg/mL A solvent system of propylene glycol and glacial acetic acid with a composition of 98.5% propylene glycol and 1.5% glacial acetic acid by weight can be prepared by adding 1.5 g of glacial acetic acid to 98.5 g propylene glycol and mixing until a uniform solution is produced. Then dissolve 2.25 g of 4-[4-[4-(hydroxydiphenylmethyl)-1-piperidinyl]-1-hydroxybutyl]-α,α-dimethylbenzeneacetic acid hydrochloride in 40 mL of the solvent system. Heat may be applied if needed to facilitate dissolution of 4-[4-[4-(hydroxydiphenylmethyl)-1-piperidinyl]-1-hydroxybutyl]-α,α-dimethylbenzeneacetic acid hydrochloride. After dissolution is complete, add a sufficient amount of the solvent system to bring the total volume of the solution to 50 mL (q.s.), to provide the oral pharmaceutical composition in solution form with a strength of 45.0 mg/mL.

EXAMPLE 3

Preparation of an Oral Pharmaceutical Composition of 4-[4-[4-(Hydroxydiphenylmethyl)-1-piperidinyl]-1-hydroxybutyl]- α,α-dimethylbenzeneacetic acid hydrochloride in Solution Form with a Strength of 67.5 mg/mL A solvent system of propylene glycol and glacial acetic acid with a composition of 98.5% propylene glycol and 1.5% glacial acetic acid by weight can be prepared by adding 1.5 g of glacial acetic acid to 98.5 g propylene glycol and mixing until a uniform solution is produced. Then dissolve 3.375 g of 4-[4-[4-(hydroxydiphenylmethyl)-1-piperidinyl]-1-hydroxybutyl]-α,α-dimethylbenzeneacetic acid hydrochloride in 40 mL of the solvent system. Heat may be applied if needed to facilitate dissolution of 4-[4-[4-(hydroxydiphenylmethyl)-1-piperidinyl]-1-hydroxybutyl]-α,α-dimethylbenzeneacetic acid hydrochloride. After dissolution is complete, add a sufficient amount of the solvent system to bring the total volume of the solution to 50 mL (q.s.), to provide the oral pharmaceutical composition in solution form with a strength of 67.5 mg/mL.

EXAMPLE 4

Preparation of an Oral Pharmaceutical Composition of 4-[4-[4-(Hydroxydiphenylmethyl)-1-piperidinyl]-1-hydroxybutyl]- α,α-dimethylbenzeneacetic acid hydrochloride in Solution Form with a Strength of 90.0 mg/mL A solvent system of propylene glycol and glacial acetic acid with a composition of 98.5% propylene glycol and 1.5% glacial acetic acid by weight can be prepared by adding 1.5 g of glacial acetic acid to 98.5 g propylene glycol and mixing until a uniform solution is produced. Then dissolve 4.50 g of 4-[4-[4-(hydroxydiphenylmethyl)-1-piperidinyl]-1-hydroxybutyl]-α,α-dimethylbenzeneacetic acid hydrochloride in 40 mL of the solvent system. Heat may be applied if needed to facilitate dissolution of 4-[4-[4-(hydroxydiphenylmethyl)-1-piperidinyl]-1-hydroxybutyl]-α, αdimethylbenzeneacetic acid hydrochloride. After dissolution is complete, add a sufficient amount of the solvent system to bring the total volume of the solution to 50.0 mL (q.s.), to provide the oral pharmaceutical composition in solution form with a strength of 90.0 mg/mL.

EXAMPLE 5

Preparation of an Oral Pharmaceutical Composition of 4-[4-[4-(Hydroxydiphenylmethyl)-1-piperidinyl]-1-hydroxybutyl]- α,α-dimethylbenzeneacetic acid hydrochloride in Solution Form with Varying Strengths In a manner analogous to the procedures described in examples 1 through 4, one of ordinary skill in the art can prepare oral pharmaceutical compositions of 4-[4-[4-(Hydroxydiphenylmethyl)-1-piperidinyl]-1-hydroxybutyl]-α,α-dimethylbenzeneacetic acid hydrochloride in solution form with varying strengths, in addition to those described previously. For example, oral pharmaceutical compositions of 4-[4-[4-(hydroxydiphenylmethyl)-1-piperidinyl]-1-hydroxybutyl]-α,α-dimethylbenzeneacetic acid hydrochloride in solution form with strengths of 112.5 mg/mL, 135 mg/ml, 157.5 mg/mL and 180 mg/mL can be prepared.

What is claimed is:

1. An oral pharmaceutical composition in solution form, comprising:
    a) a therapeutically effective amount of a piperidinoalkanol compound or a pharmaceutically acceptable salt thereof; and
    b) a suitable solvent system, the solvent system comprising about 95.0% to about 99.9% propylene glycol by weight of the solvent system and about 0.1% to about 5.0% glacial acetic acid by weight of the solvent system.

2. The oral pharmaceutical composition in solution form according to claim 1 wherein said solvent system comprises,
    a) about 98.0% to about 99.0% propylene glycol by weight of the solvent system; and
    b) about 1.0% to about 2.0% glacial acetic acid by weight of the solvent system.

3. The oral pharmaceutical composition in solution form according to claim 1 wherein said solvent system comprises,
    a) about 98.5% propylene glycol by weight of the solvent system; and
    b) about 1.5% glacial acetic acid by weight of the solvent system.

4. The oral pharmaceutical composition in solution form according to either one of claims 1, 2, or 3 wherein said piperidinoalkanol compound is of the formula

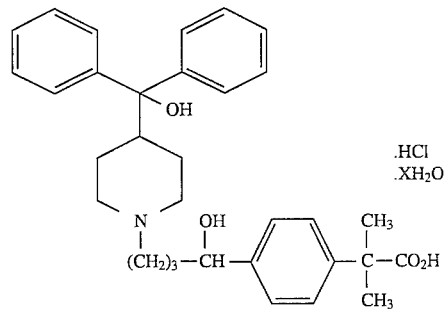

wherein X is a number ranging from about zero to 5, and the individual optical isomers thereof.

5. The oral pharmaceutical composition in solution form according to claim 4 wherein X is zero.

6. The oral pharmaceutical composition in solution form according to claim 5 wherein 4-[4-[4- (hydroxydiphenylmethyl)-1-piperidinyl]-1-hydroxybutyl]-α,α-dimethylbenzeneacetic acid hydrochloride is present in an amount of about 0.01 mg/mL to about 188 mg/mL.

7. The oral pharmaceutical composition in solution form according to claim 5 wherein 4-[4-[4- (hydroxydiphenylmethyl)-1-piperidinyl]-1-hydroxybutyl]-α,α-dimethylbenzeneacetic acid hydrochloride is present in an amount of about 22.5 mg/mL.

8. The oral pharmaceutical composition in solution form according to claim 5 wherein 4-[4-[4-(hydroxydipheny methyl)-1-piperidinyl]-1-hydroxybutyl]-α,α-dimethylbenzeneacetic acid hydrochloride is present in an amount of about 45.0 mg/mL.

9. The oral pharmaceutical composition in solution form according to claim 5 wherein 4-[4-[4- (hydroxydiphenylmethyl)-1-piperidinyl]-1-hydroxybutyl]-α,α-dimethylbenzeneacetic acid hydrochloride is present in an amount of about 67.5 mg/mL.

10. The oral pharmaceutical composition in solution form according to claim 5 wherein 4-[4-[4-(hydroxydiphenylmethyl) -1-piperidinyl]-1-hydroxybutyl]-α,α-dimethylbenzeneacetic acid hydrochloride is present in an amount of about 90.0 mg/mL.

* * * * *